(12) United States Patent
Tornier et al.

(10) Patent No.: US 6,540,770 B1
(45) Date of Patent: Apr. 1, 2003

(54) REVERSIBLE FIXATION DEVICE FOR SECURING AN IMPLANT IN BONE

(75) Inventors: Alain Tornier, Saint Ismier (FR); Francois Bonnomet, Strasbourg (FR)

(73) Assignee: Tornier SA, Saint Ismier (FR)

( * ) Notice: Subject to any disclaimer, the term of this patent is extended or adjusted under 35 U.S.C. 154(b) by 0 days.

(21) Appl. No.: 09/673,791

(22) PCT Filed: Apr. 21, 1999

(86) PCT No.: PCT/FR99/00940
§ 371 (c)(1),
(2), (4) Date: Feb. 8, 2001

(87) PCT Pub. No.: WO99/53843
PCT Pub. Date: Oct. 28, 1999

(30) Foreign Application Priority Data

Apr. 21, 1998 (FR) ............................................. 98 05202

(51) Int. Cl.⁷ ............................................. A61B 17/04
(52) U.S. Cl. ..................................................... 606/232
(58) Field of Search ........................... 606/232, 72, 74, 606/75; 24/297, 324, 662; 411/34, 36, 37, 38, 43, 59, 60, 61

(56) References Cited

U.S. PATENT DOCUMENTS

| | | | |
|---|---|---|---|
| 4,268,001 A | * 5/1981 | Nicholson et al. ............. 606/72 |
| 5,248,231 A | * 9/1993 | Denham et al. ............... 411/43 |
| 5,326,205 A | * 7/1994 | Anspach, Jr. et al. .......... 411/43 |
| 5,472,452 A | 12/1995 | Trott |
| 5,480,403 A | * 1/1996 | Lee et al. ...................... 606/72 |
| 5,486,197 A | * 1/1996 | Le et al. ...................... 606/232 |
| 5,501,695 A | 3/1996 | Anspach, Jr. et al. |
| 5,522,845 A | * 6/1996 | Wenstrom, Jr. ............... 606/232 |
| 5,643,321 A | * 7/1997 | McDevitt ..................... 606/232 |
| 5,649,963 A | 7/1997 | McDevitt |
| 5,725,541 A | * 3/1998 | Anspach, III et al. ......... 606/151 |
| 5,741,282 A | * 4/1998 | Anspach, III et al. ......... 606/151 |
| 5,814,071 A | * 9/1998 | McDevitt et al. ............. 606/232 |
| 6,146,406 A | * 11/2000 | Shluzas et al. ............... 606/232 |
| 6,241,732 B1 | * 6/2001 | Overaker et al. .............. 606/72 |
| 6,328,758 B1 | * 12/2001 | Tornier et al. ............... 606/232 |

FOREIGN PATENT DOCUMENTS

GB    2173565 A    10/1986

* cited by examiner

*Primary Examiner*—John J. Calvert
*Assistant Examiner*—Alissa L. Hoey
(74) *Attorney, Agent, or Firm*—Dowell & Dowell, P.C.

(57) ABSTRACT

A device for fixing an implant in a patient's bone which includes an expanding element which is limited in it's plastic deformation when a force is applied for fixing the implant in the bone, such that the expanding element is reversible when another force is applied for removing the implant from the bone.

11 Claims, 7 Drawing Sheets

REVERSIBLE FIXATION DEVICE FOR SECURING AN IMPLANT IN BONE

CROSS REFERENCE TO RELATED APPLICATIONS

This application is a National Phase Application of International Application PCT/FR99/00940, filed Apr. 21, 1999 which claims priority from French Patent Application 98 05202, filed Apr. 21, 1998.

BACKGROUND OF THE INVENTION

1. Field of the Invention

The present invention relates to a reversible device for the fixation of an implant in the bone of a patient.

2. Brief Description of the Related Art

U.S. Pat. No. 5,501,695 discloses a device for the fixation of a suture anchor in the bone, which device consists of two separate parts.

The fixation device comprises a first firmly attached external, cylindrical element affixed to fixation prongs that are separated from each other by grooves running parallel to the longitudinal axis of said device. The first element accommodates on its inside a second element of deformation that interacts with the free extremity of the fixation prongs.

The second element of irreversible deformation is firmly affixed through a fracture zone to a tie rod which enables the surgeons, after having inserted the suture anchor into a hole previously drilled in the bone, to have the second element slide inside of the first one to axially deform the fixation prongs in the area of the spongy bone.

Since the tractile force is sufficient to deform the fixation prongs, the rod separates from the second element by an irreversible break.

It can be noted that the prongs deform laterally following a direction essentially perpendicular to the longitudinal axis of the suture anchor in order to permanently fasten the latter inside of the bone.

Lastly, to the first element is firmly affixed at one its extremities a flange that comes to rest against the cortical bone and into which are drilled a number of holes for the fastening of the suture threads by the surgeon.

The above-described fixation device presents some disadvantages, namely, that it does not allow the removal of the suture anchor from the bone without causing a complete destruction of the bone and of the bone to which it is attached. In fact, the suture anchor is not provided with any means of removal that would allow it to be disengaged from the bone without causing any damage to it.

Moreover, beyond the fracture zone of the second element, the fixation device is not provided with means that limit the displacement of said element to prevent the fixation prongs from breaking in an abnormal manner under the effects of the tractile force.

Also, U.S. Pat. No. 5,472,452 discloses a fixation device for a suture anchor provided with expansion means that are plastically deformed by means of an appliance.

This fixation device is provided with expansion means that are reversible within the direction of the stress of the appliance and, in particular, of the structure of the implement whose thruster presents an inclined plane allowing the means of expansion to descend into the body of the suture anchor in order to be able to remove it.

This fixation device relates to a suture anchor that is not provided with means to delimit the plastic deformation of the expansion means when a tractile force is applied, in order to prevent an abnormal rupture or an excessive plastic deformation which would render the fixation device irreversible.

Also known are other anchor fixation devices, either by force or by screws, that do not allow a removal of the implant without causing damage to the bone.

The present invention has the aim to specifically remedy these disadvantages.

SUMMARY OF THE INVENTION

The fixation device in accordance with the present invention has as object that of being reversible, thus allowing its removal from the bone without having to drill a hole of greater diameter than that of the deformed prongs.

The fixation device in accordance with the present invention is provided with expansion means that are reversible in the direction of the force in order to allow either the fixation of the implant to the bone or its removal.

The fixation device in accordance with the present invention comprises expansion means whose plastic deformation is limited by stop means when a force is applied for the fixation of the implant to the bone, so that said expansion means become reversible when another force is applied enabling the removal of the implant from the bone.

The fixation device in accordance with the present invention comprises expansion means that are limited by stop means in their plastic deformation when a force is applied that allows the fixation of the implant to the bone, so that these expansion means be reversible when another force is applied that allows the removal of said implant from the bone.

The fixation device in accordance with the present invention is provided with expansion means that consist, on the one hand, of a cylindrical section provided with an internal threaded borehole, at least two fixation prongs arranged parallel to the longitudinal axis and on the extension of the cylindrical section, and at least two stops inserted between each prong that limit the plastic deformation of said prongs, and a conical point with a threaded blind hole on its inside.

The fixation device in accordance with the invention is provided at the level of its conical point with a threaded blind hole intended for a threaded rod of an attachment to deform the fixation prongs subjected to a tractile force in a direction essentially parallel to the longitudinal axis.

The fixation device in accordance with the present invention is provided in its cylindrical section with a threaded borehole that is intended for a threaded hollow rod of another attachment, while another rod sliding inside the first one comes to rest against the bottom of the threaded blind hole to open, under the effect of a thrust force, the fixation prongs in a position essentially identical to the original one in order to be able to remove the implant from the bone.

The below description, taking into account the accompanying drawings, given as not limiting examples, allows a better understanding of the invention, of its characteristics and the advantages it may provide.

Figure 1:
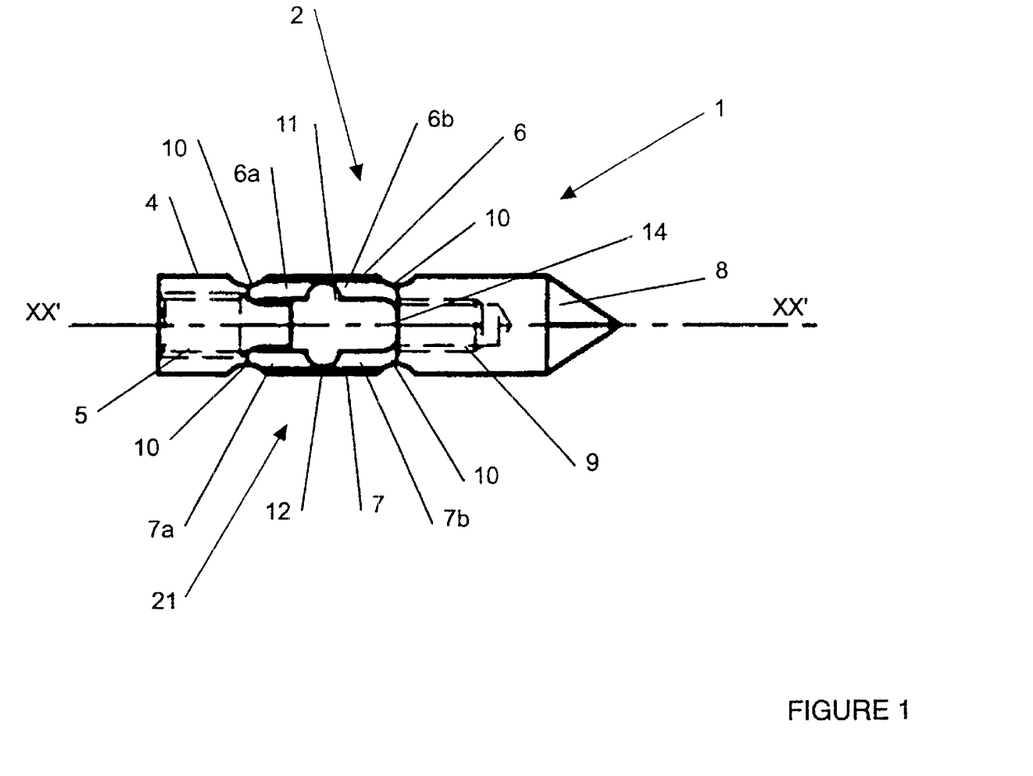
FIG. 1 is a view illustrating an implant of whatsoever shape provided with a fixation device in accordance with the present invention.

FIG. 1 illustrates an implant 1 that can be of whatsoever shape and that is provided with a fixation device 2 comprising expansion means 21 that are reversible, which fact enables the surgeon to operate anew with the implant 1 without causing much damage to the bone 3.

DESCRIPTION OF THE PREFERRED EMBODIMENT

The fixation device 2 comprises a hollow cylindrical section 4, on the inside of which is drilled threaded borehole 5.

The cylindrical section 4 of the fixation device 2 is extended by at least two fixation prongs 6, 7 that, prior to deformation, are parallel to the longitudinal axis XX' of the cylindrical section 4.

The fixation device 2 comprises on the extension of the prongs 6 and 7 a conical point 8, facilitating the insertion of the implant into the bone 3.

The cylindrical section 4 of the fixation device 2 is provided on its inside with a threaded borehole 9 on the longitudinal axis XX' that opens, on the one hand, to the outside of the implant 1 and, on the other hand, between the fixation prongs 6 and 7.

Also, the conical point 8 of the fixation device 2 is provided on its inside with a threaded blind hole 9 that opens between the fixation prongs 6 and 7, which hole is drilled on the same longitudinal axis XX' as that of the borehole 5.

Further, the diameter of the threaded borehole 5 is greater than that of the threaded blind hole 9.

The prongs 6 and 7 are attached to the cylindrical section 4 and to the point 8 by means of bending fasteners 10 oriented in direction towards the center of the fixation device 2, allowing the deformation of said prongs under the effects of a tractile force.

The prongs 6 and 7 are provided in their center with bending fasteners 11, 12, respectively, that are inverted with respect to the ones 10, so that each prong is constituted by two segments 6a, 6b and 7a, 7b.

It can be observed that the bending fasteners 10, 11 and 12 have an arc of a circle shape of constant radius.

Between each prong 6 and 7 is provided a stop 13 attached to the cylindrical section 4 and oriented in direction towards the conical point 8. Each stop 13 runs parallel to the longitudinal axis XX' and has a length that depends on the deformation of the prongs 6 and 7 one wishes to obtain.

In fact, the deformation of the prongs 6 and 7 is limited by the stops 13 that come to rest against a surface 14 of the conical point 8. The surface 14 is arranged on a plane that is perpendicular to that of the axis XX'.

Figure 2A:
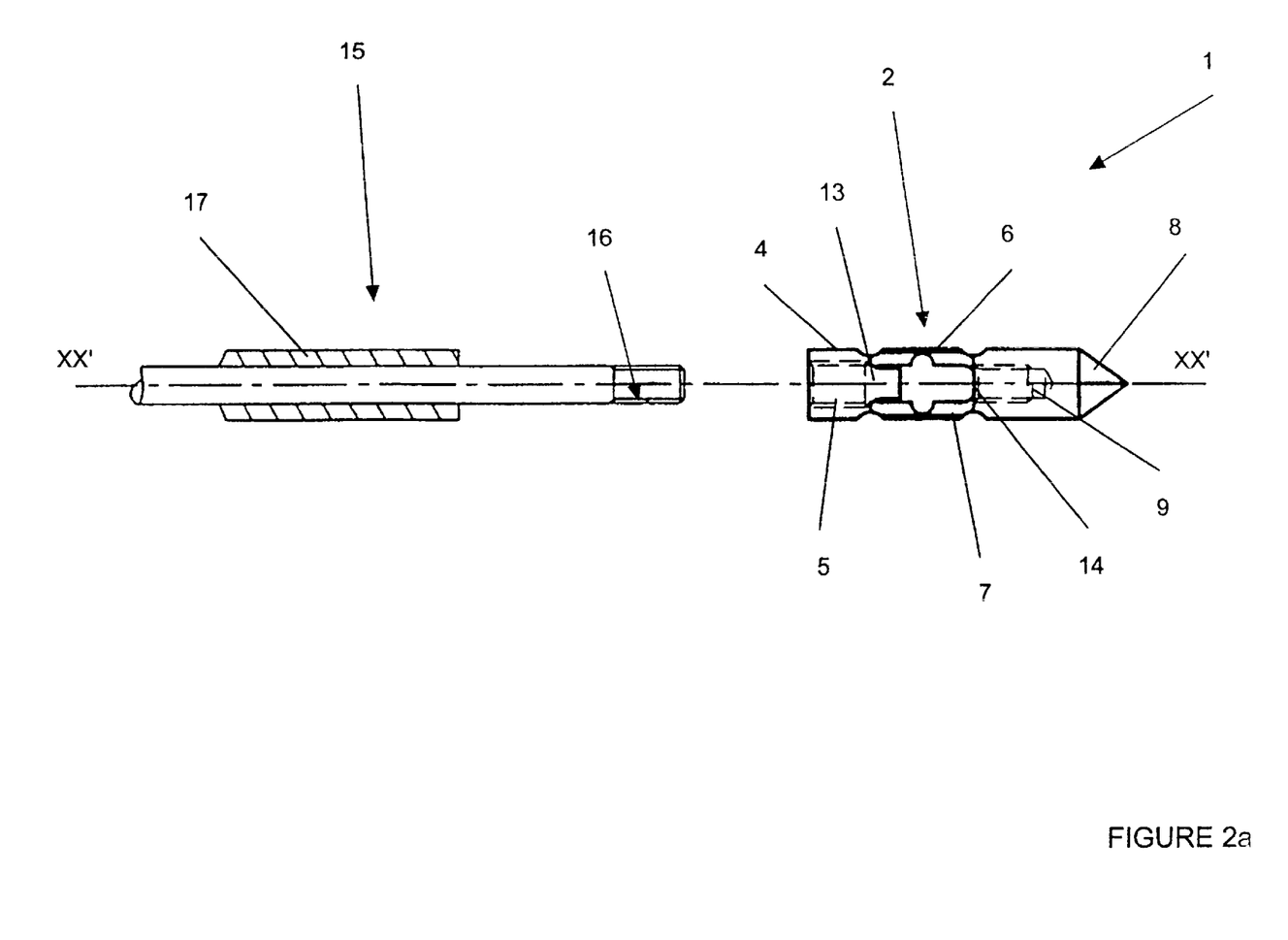
FIGS. 2a to 2c are diagrammatic views illustrating the placing of the implant in a bone by means of the fixation device in accordance with the invention.
Figure 2B:
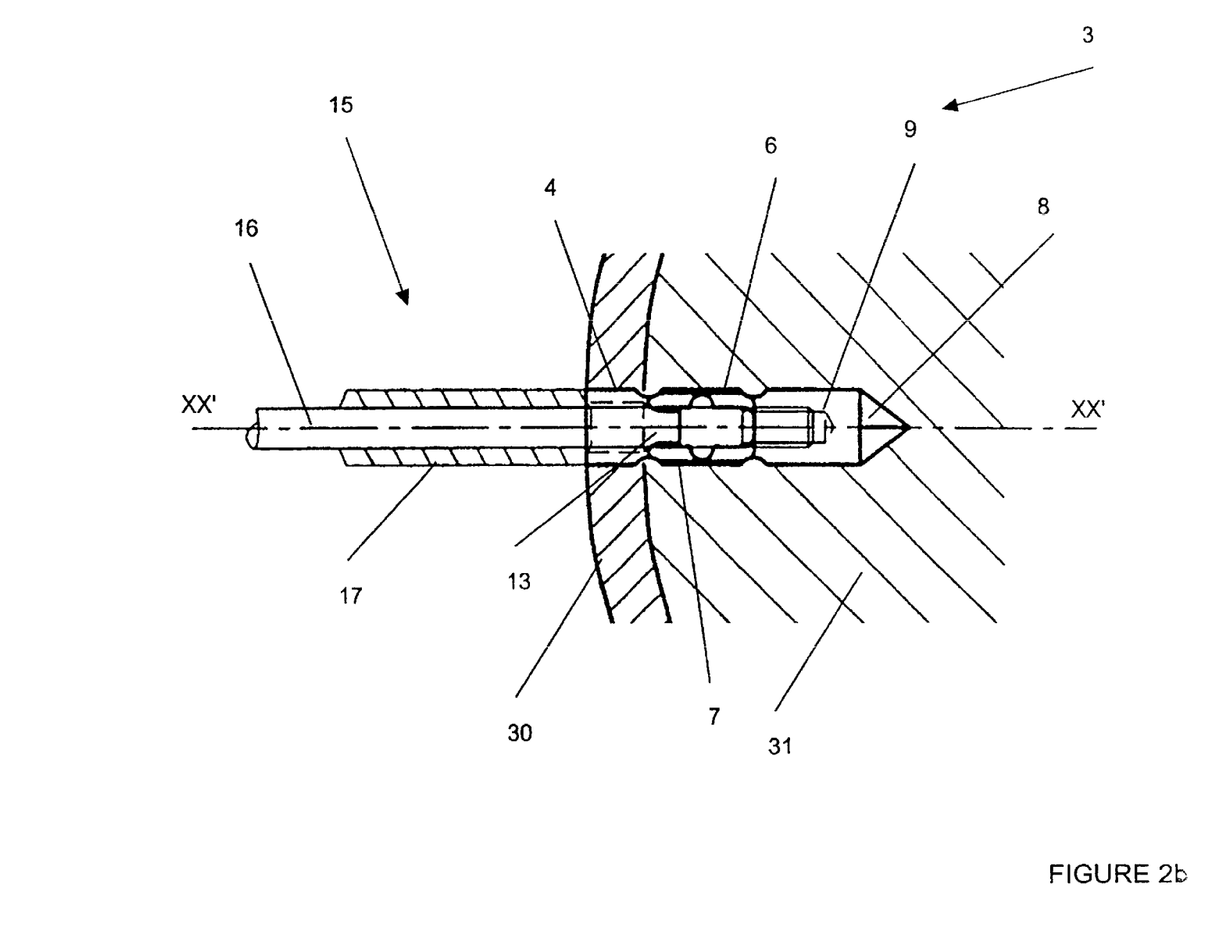
Figure 2C:
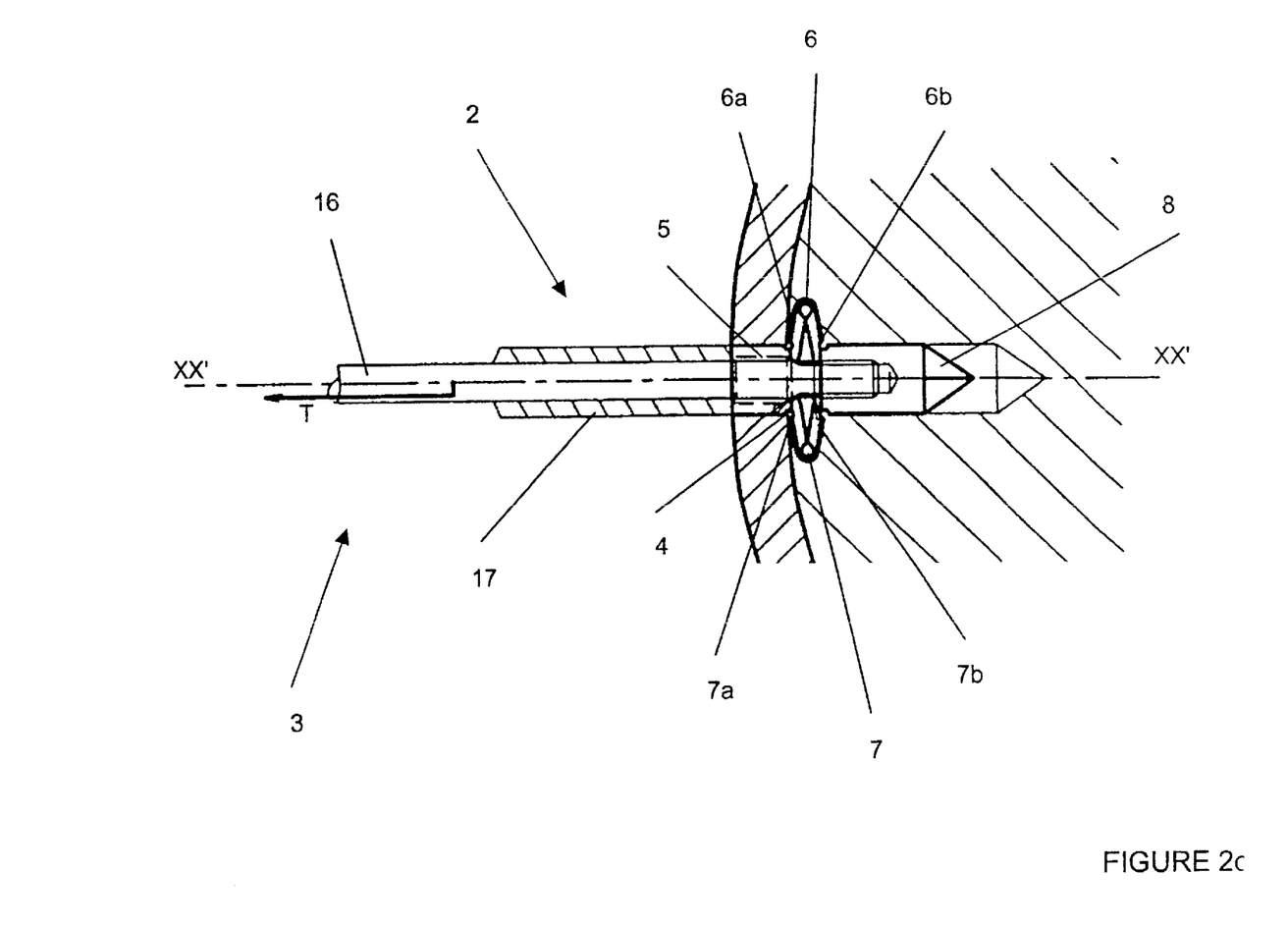

In FIGS. 2a to 2c are illustrated the various stages of the placing inside of bone of the implant 1, provided with the fixation device 2.

In FIG. 2a is illustrated the implant 1 to which is affixed an attachment 15 for the setting in place that, by way of example, is constituted by a rod 16 that traverses the inside of the fixation device 2 to be screwed into the blind hole 9 of the conical point 8. The rod 16 is attached to a sleeve 17 that comes to rest against the cylindrical section 4.

In FIG. 2b is illustrated the implant 1 that is inserted into the surgical location by means of the attachment 15.

The setting in place of the implant 1 in the bone 3 is effectuated either by force or by rotation, or with the aid of a preliminary hole drilled into the cortical bone 30 and the spongy bone 31.

In FIG. 2c is illustrated the deformation of the fixation device 2 and, in particular, of the prongs 6 and 7 inside the spongy bone 31 when the rod 16 of the attachment 15 is subjected to a tractile force T. Thus, the rod 16 displaces horizontally in the direction of the axis XX' while the sleeve 17 continues to rest against the cylindrical section 4.

The deformation of the prongs 6 and 7 is limited until the surface 14 of the conical point 8 comes into contact with the stops 13.

The prongs 6 and 7 are deformed, under the effect of the compression stress of the tractile force T applied to the rod 16 of the attachment 15, according to the shape of the fasteners 10, 11 and 12, so that the segments 6a, 6b and 7a, 7b are oriented towards the outside of the implant 1 and in a direction essentially perpendicular to the axis XX'.

It can be observed that the fixation of the implant 1 in the spongy bone 31 is effectuated by the deformation of the prongs 6 and 7 until the segments 6a and 7a come into contact with the internal surface of the cortical bone 30.

Then, the rod 17 is unscrewed from the attachment 16 in order to release the implant 1.

Figure 3A:
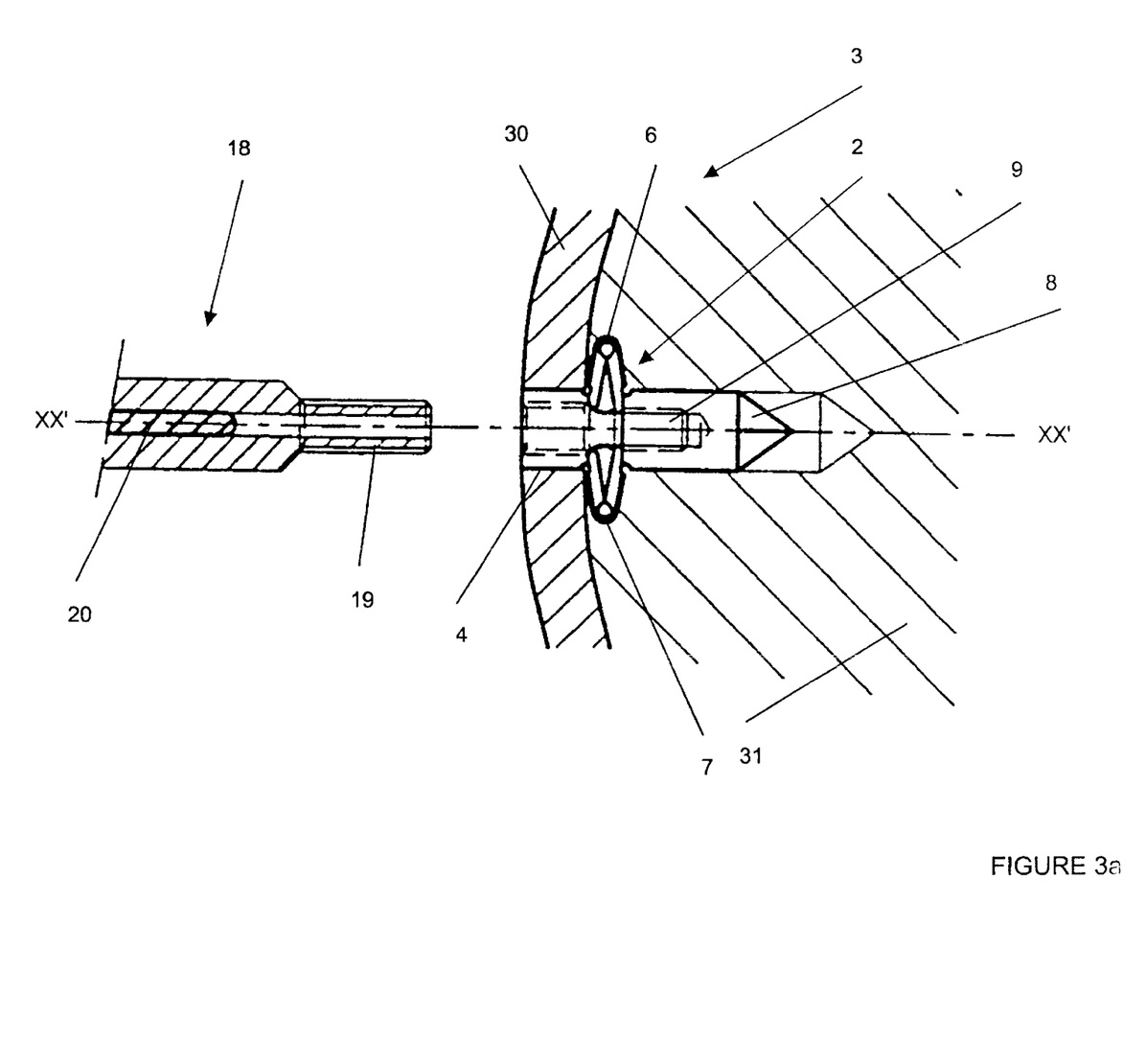
FIGS. 3a to 3c are diagrammatic views illustrating the removal of the implant from the bone due to the reversibility of the fixation device in accordance with the present invention.
Figure 3B:
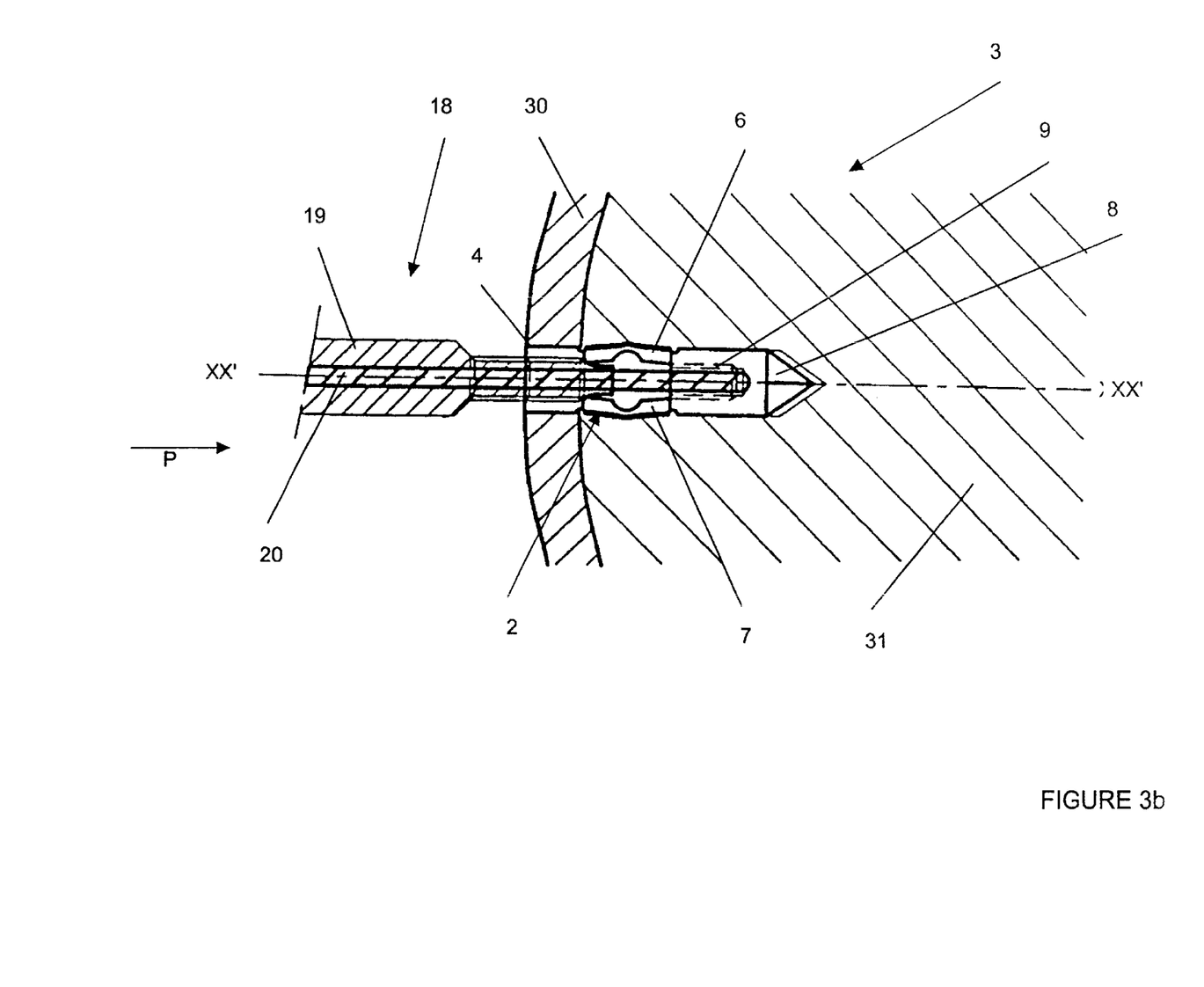
Figure 3C:
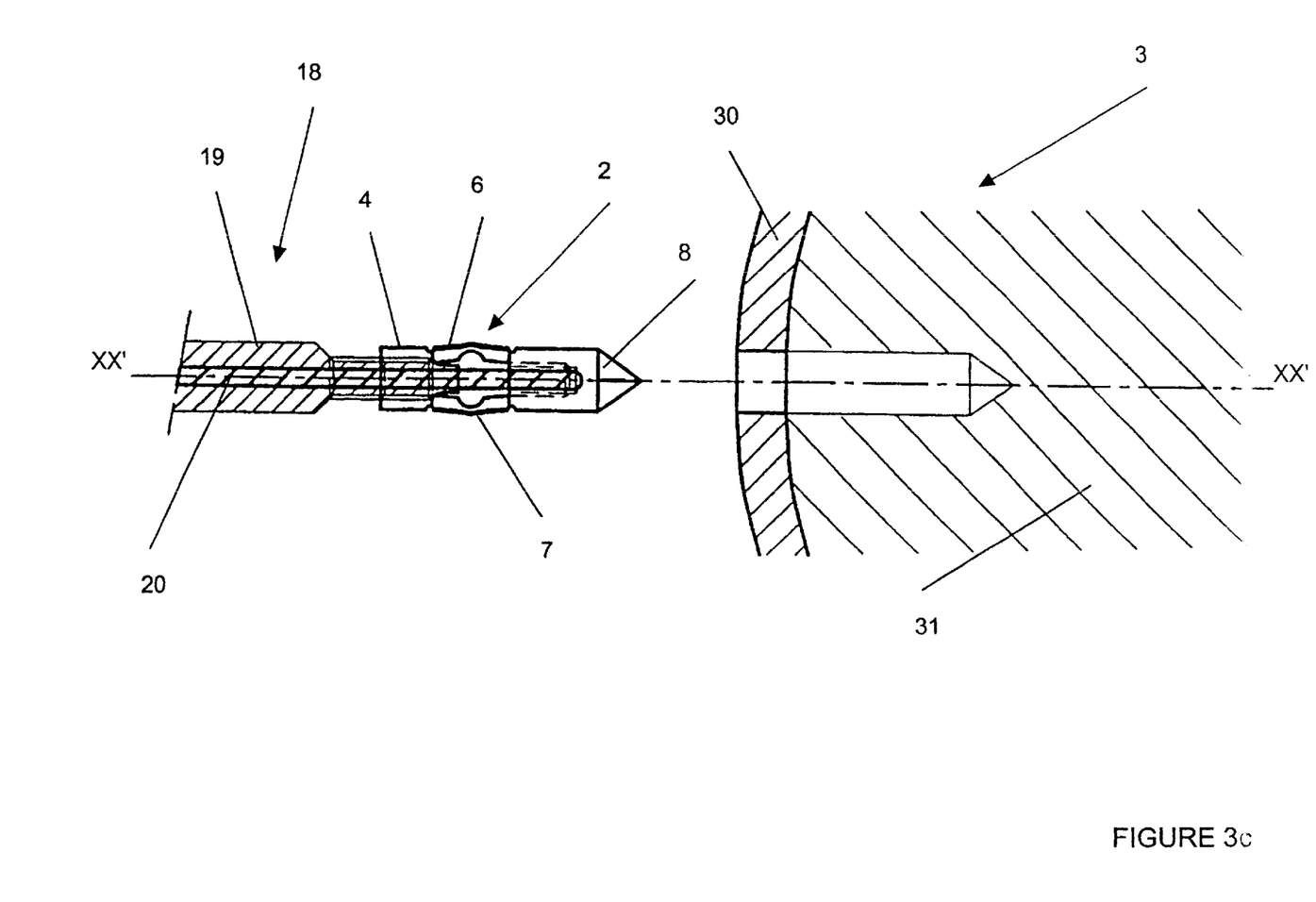

In FIGS. 3a to 3c are illustrated the various stages of the removal of the implant 1 from the bone 3 by means of another attachment 18 allowing the reversibility of the fixation device 2.

The attachment 18 is provided with a hollow rod 19 that is screwed into the threaded borehole 5 of the cylindrical section 4, while another rod 20 sliding in the first one comes to rest against the bottom of the blind hole 9 drilled in the conical point 8 (FIG. 3b).

The rod 20 is subjected to a thrust force P parallel to the axis XX' in order to open the prongs 6 and 7 (FIG. 3c). The shape of the fasteners 10, 11 and 12 allows to return the fixation device 2 to a shape similar to the original one.

When the fixation device 2 has returned to an elongated position, by means of the attachment 18, the surgeon can remove the implant 1 from the bone 3 without having to drill a hole with an approximate diameter of the deformed prongs.

The above described fixation device has been applied by way of embodiment to a suture anchor. Evidently, and without changing the object of the present invention, it is intended that the reversible fixation device be applied to any type of implant to be inserted into the bone of a patient.

What we claim is:

1. A fixation device for an implant in a bone of a patient, which includes an expansion means (21) having a plastic deformation which is limited when a force (T) is applied for fixation of the implant to the bone, and said expansion means being reversible when another force (P) is applied thereto which thereby permits removal of the implant from the bone.

2. The fixation device of claim 1 including stop means for limiting the plastic deformation of the expansion means (13) when the force (T) is applied for fixation of the implant to the bone.

3. The fixation device of claim 1, wherein said expansion means includes a cylindrical section (4) in which is provided an internal threaded borehole (5), at least two fixation prongs (6, 7) arranged parallel to a longitudinal axis (XX') of, and extending from, cylindrical section (4) prior to the plastic deformation, at least two stops (13) inserted between said prong (6, 7) for limiting the plastic deformation of said prongs, and a conical point (8) having a threaded blind hole (9).

4. The fixation device of claim 3, wherein said at least two fixation prongs (6, 7) are attached to said cylindrical section (4) and to said conical point (8) by first bending fasteners (10) oriented towards a center of the fixation device.

5. The fixation device of claim 3, wherein each of said at least two fixation prongs (6, 7) is provided generally centrally with second bending fasteners (11, 12), respectively, which are inverted with respect to said first bending fasteners (10) so that each of said at least two fixation prongs is constituted by two identical segments (6a, 6b; 7a, 7b).

6. The fixation device of claim 3, wherein said internal threaded borehole (5) and said threaded blind hole (9) are axially aligned on the longitudinal axis (XX') and have different diameters.

7. The fixation device of claim 3, wherein said at least two stops (13) extend parallel to the longitudinal axis (XX') and have lengths which determine the extent of plastic deformation of said at least two fixation prongs (6, 7).

8. The fixation device of claim 3, wherein said at least two stops (13) rest against a surface (14) of said conical point (8) that is perpendicular to the longitudinal axis (XX') when said at least two fixation prongs (6,7) have been deformed.

9. The fixation device of claim 3, wherein said threaded blind hole (9) is of a size to receive a threaded rod (16) of an attachment member (15) which is used to deform, under the force (T), said at least two fixation prongs (6, 7) in a direction essentially perpendicular to the longitudinal axis (XX').

10. The fixation device of claim 3, wherein said threaded borehole (5) is of a size to receive a hollow threaded rod (19) of a first attachment (18) and wherein a rod (20) is slidable inside said first attachment so as to rest at a bottom of the threaded blind hole (9) to thereby open, under force (P), aid at least two fixation prongs (6, 7) to a position essentially identical to an original non deformed position to thereby permit removal of the implant from the bone.

11. A fixation device for securing an implant to a bone which includes a hollow body having expansion means (6, 7) which, under an effect of a first external tractive force (T) for the fixation of the device to the bone, are limited by stop means (13) in a plastic deformation, and the deformation of said expansion means (6, 7) being reversible by an external thrust force (P) applied thereto, which allows the removal of the implant from the bone.

* * * * *